United States Patent [19]

Saruhashi et al.

[11] Patent Number: 4,729,948

[45] Date of Patent: Mar. 8, 1988

[54] DRY ANALYTICAL ELEMENT FOR α-AMYLASE

[75] Inventors: Masakuni Saruhashi; Isao Haga; Morio Kobayashi; Kazumi Arai, all of Hino, Japan

[73] Assignee: Konishiroku Photo Industry Co., Ltd., Tokyo, Japan

[21] Appl. No.: 647,679

[22] Filed: Sep. 5, 1984

[30] Foreign Application Priority Data

Sep. 12, 1983 [JP] Japan .................. 58-166530

[51] Int. Cl.[4] .............................. C12Q 1/40
[52] U.S. Cl. ...................... 435/22; 435/805
[58] Field of Search .................. 435/22, 805; 428/402.24; 252/408.1; 422/56, 57

[56] References Cited

U.S. PATENT DOCUMENTS

| | | | |
|---|---|---|---|
| 3,888,739 | 6/1975 | Whetzel et al. | 435/22 |
| 3,992,158 | 11/1976 | Przybylowicz et al. | 435/11 |
| 4,066,509 | 1/1978 | Ceska | 435/18 |
| 4,144,306 | 3/1979 | Figueras | 435/22 |
| 4,356,149 | 10/1982 | Kitajima et al. | 435/12 |

FOREIGN PATENT DOCUMENTS 2085159  4/1982  United Kingdom .

OTHER PUBLICATIONS

Lathia, D. et al., Clinica. Chimica Acta, 82, (1978), pp. 209-214.

Primary Examiner—Robert J. Warden
Assistant Examiner—Randall E. Deck
Attorney, Agent, or Firm—Frishauf, Holtz, Goodman & Woodward

[57] ABSTRACT

There is disclosed a dry analytical element for α-amylase in a fluid sample which comprises the analytical element including a starch capable of forming a complex with iodine, an iodine compound and an oxidizing agent, and the iodine compound and the oxidizing agent are disposed in the element so that iodine may be liberated therefrom when the fluid sample is brought into contact with the analytical element.

The analytical element of this invention enables an easy, prompt and accurate dry quantitative analysis of a component in a fluid sample, especially a biological fluid sample by the use of visible light with the aid of a spectrophotometer.

21 Claims, 3 Drawing Figures

DRY ANALYTICAL ELEMENT FOR α-AMYLASE

BACKGROUND OF THE INVENTION

This invention relates to an analytical element, particularly an analytical element for analyzing predetermined specific components in a fluid. More specifically, it relates to an analytical element for detecting and quantitatively analyzing α-amylase in a biological fluid sample.

Heretofore, many methods for analyzing a specific component in a fluid sample have been developed. These methods can be roughly classified into a reaction system (wet chemistry) where a reaction is carried out in a solution, and another reaction system (dry chemistry) where a reaction is carried out in a solid phase carrier. They have problems in operating characteristics or measuring accuracy.

Besides the conventional methods mentioned above, there are known multi-layer analytical elements in which the dry chemistry easy to operate is employed and which has a quantitative character. Such multi-layer analytical elements are disclosed in, for example, Japanese Patent Publication No. 21677/1978, and Japanese Provisional Patent Publications No. 164356/1980, No. 125847/1982, No. 197466/1982 and No. 90167/1983.

In the elements disclosed therein, all the reagents necessary for an analytical reaction are incorporated into one analytical element, and the concentration of a specific substance in a sample can be determined as follows: A certain amount of a serum or a whole blood is dropped onto the above-mentioned element; the latter is maintained at a selected temperature for a certain period of time; the determination of a reflected concentration is then carried out from a support side of the element; and on the basis of the reflected concentration, the concentration of the specific material is finally determined.

The aforesaid method has a higher analytical accuracy as compared with a conventional test paper type element, and possesses a reliability equal to or higher than the wet chemistry without needing to previously prepare any reagent.

The analytical element for analyzing α-amylase which has such characterictics is disclosed in Japanese Provisional Patent Publication No. 131089/1978. The disclosed analytical element comprises a light-transmissive and liquid-impervious support, and, for example, a registration layer, a blocking layer and a diffusion-reagent layer mentioned above is composed of an insoluble starch chemically bonded to a dye and an isotropically porous matrix; the blocking layer is composed of light-reflective titanium dioxide and a hydrophilic binder; and the registration layer is composed of a hydrophilic binder and a mordant.

According to the above-mentioned constitution, α-amylase in the fluid sample will break an α-1,4-bond of the dye-bonded insoluble starch in the diffusion-reagent layer, and the resulting diffusive fragments of the dye-bonding insoluble starch will permeate through the blocking layer and will bond to the mordant of the registration layer in order to give a dye.

In such an analytical element for analyzing α-amylase, there is utilized a so-called dystuff-bonded starch method (a chromogenic method) which is a kind of solution process. Originally, the dyestuff-bonded starch method comprises causing α-amylase in a specimen material to act on the insoluble dyestuff-bonding starch which is a substrate; filtering resultant fragments of a soluble dyestuff-bonding starch having a low-molecular weight; and carrying out a colorimetry to determine an activity of the α-amylase. It is definite that in this method, the separation between the unreacted insoluble dyestuff-bonding starch and the soluble dyestuff-bonding starch which is the reaction product is important.

In the above-mentioned analytical element for α-amylase, this separation depends on the diffusion of the fragments of the soluble dyestuff-bonding starch, which is the reaction product, from the diffusion-reagent layer to the registration layer through the blocking layer and the mordanting in the registration layer, but the diffusion of such a macromolecule is greatly affected by components in a specimen material. For this reason, the above-mentioned analytical element has disadvantages such as the formation of an non-uniform color density and the occurence of rings due to a chromatic phenomenon, and it is thus considered that the analytical element just described is noticeably poor in accuracy. Further, since the unreacted substrate and the reaction product have the same dyestuff, the blocking layer for blocking the color of the unreacted substrate must be disposed between the registration layer and the diffusion-reagent layer in order to distinguish these two colors.

In Japanese Provisional Patent Publication No. 40649/1982, there is disclosed other analytical element for α-amylase. This analytical element comprises a light-transmissive and liquid-impervious support, and a second reagent layer and a first reagent layer provided in turn on the support. The first reagent layer above includes an undiffusible starch having dyestuff-forming reactive group, and the second reagent layer contains a chromogen compound.

According to the above-mentioned analytical element having such a constitution, the undiffusible starch having dyestuff-forming reactive group will be decomposed to change into a lower-molecular diffusible starch having dyestuff-forming reactive group by the α-amylase in a fluid sample, and the diffusible starch will permeate into the second layer and will react with the chromogen compound in order to form a dyestuff. For the formed dyestuff, a colorimetry will then be carried out to quantitatively measure the α-amylase.

The substrate having the dyestuff-forming reactive groups which is present in the first reagent layer is insoluble, therefore it will not permeate into the second reagent layer. In consequence, the unreacted substrate will not react with the undiffusible chromogen compound present in the second reagent layer so as to develop a color. Accordingly, this analytical element advantageously needs no blocking layer particularly which is essential in the analytical element for α-amylase disclosed in Japanese Provisional Patent Publication No. 131089/1978 referred to hereinbefore.

However, the analytical element for α-amylase disclosed in Japanese Provisional Patent Publication No. 40649/1982 is constitutionally the same as the analytical element disclosed in Japanese Provisional Patent Publication No. 131089/1978 in that the undiffusible substrate contained in the first reagent layer will be decomposed to change into the diffusible reaction product by the action of the α-amylase and the resulting reaction product will permeate into the second reagent layer. The aforesaid reaction product comprises macromolecules including several or dozens of glucose units, though being diffusible. Therefore, its diffusion from the first reagent layer to the second reagent layer will be, needless to say, non-uniform. In addition thereto, the reaction of the dyestuff-forming reactive groups in the reaction product of the substrate with the chromogen compound in the second reagent layer will be carried out in the noticeably scattering manner. It is thus fair to say that the aforementioned analytical element for α-amylase is remarkably poor in accuracy.

The α-amylase analysis based on the solution method in which a starch-iodine reaction process is employed is simple and convenient, but it has faults such as the deterioration of the starch by microorganism and the sublimation of the iodine, and also when it is used, much attention must be paid to the handling of an iodine solution which is corrosive.

Thus, the development of multi-layer analytical elements is now desired which are easy to operate and which are high in the reliability of a measuring accuracy and the like.

SUMMARY OF THE INVENTION

Accordingly, an object of this invention is to provide an analytical element for α-amylase which is excellent in measuring accuracy and wich is easy to operate.

The present inventors have intensively conducted research on such an analytical element, and finally have found that the above-mentioned drawbacks can be overcome by an analytical element having the following constitution.

Namely, generally speaking, this invention is directed to a dry analytical element for analyzing α-amylase in a fluid sample, which is characterized in that the analytical element includes a starch capable of forming a complex with iodine, an iodine compound and an oxidizing agent, and the iodine compound and the oxidizing agent are disposed in the element so that iodine may be liberated therefrom when the fluid sample is brought into contact with the analytical element.

DESCRIPTION OF THE PREFERRED EMBODIMENTS

To say more specifically, the iodine will form an iodine-starch complex together with the starch, and this complex is an inclusion compound. Color tones of the complex will be blue when the number of glucose molecules constituting the starch is 30 or more, will be red when the number thereof is 8 to 12, and will be colorless when the number thereof is 4 to 6 or less. On the other hand, the starch will be hydrolyzed by the action of the α-amylase in order to form a lower-molecular starch, i.e. an oligosaccharide. When the latter is reacted with the iodine, an iodine-starch complex will be formed, and the color of the thus formed complex will change from blue to bluish purple, purple, reddish purple, orange and yellow in compliance with the activity of the α-amylase.

The analytical element according to this invention makes use of such a color change, and a quantitative determination of the α-amylase can be carried out by measuring a reflective optical density at a certain wavelength, e.g., $\lambda = 660$ nm.

The starches used in this invention are preferably those which will be water soluble or will be dissolved when boiled, such as soluble starches, amylose, and the like. More preferable starches are amyloses which have a uniform polymerization degree and have a polymerization degree of 30 or more.

The amount of the starch included in the analytical element of this invention is within the range of about 0.1 to about 50 $g/m^2$, preferably within the range of 0.5 to 10 $g/m^2$.

In the analytical element according to this invention, as a layer including the starch, any one is acceptable so long as it can receive a macromolecule such as the α-amylase in a fluid sample, and this layer may be disposed at any position so long as it can receive such a macromolecule as α-amylase.

The iodine compounds contained in the analytical element of this invention include all iodine compounds, but the preferable iodine compounds are those which are neutral when in the condition of aqueous solutions, and the particularly preferable iodine compounds are iodines of alkali metals (e.g., tetraalkylammonium iodide such as tetramethylammonium iodide and tetraethylammonium iodide).

As the oxidizing agent included in the analytical element of this invention, any oxidizing agent may be acceptable so long as it can generate iodine by reacting with the above-mentioned iodine compound, but the oxidizing agents which can accomplish the reaction under neutral conditions are preferable, and potassium peroxodisulfate and sodium tosylchloramide are particularly preferable.

Each content of the iodine compound and the oxidizing agent included in the analytical element of this invention depends on a desired amount of the generated iodine, which iodine amount is within the range of 0.0001 to 0.1 mole/$m^2$, preferably 0.001 to 0.03 mole/$m^2$. The content of the iodine compound is, in terms of iodine ion, three times or more as much as the desired equivalent of the iodine, preferably 3 to 50 times as much as the same. Therefore, the content of the iodine compound in the analytical element of this invention is, in terms of iodine ion, within the range of about 0.0003 to about 5 moles/$m^2$, preferably 0.003 to 1.5 moles/$m^2$. Further, the content of the oxidizing agent in the analytical element of this invention is one or more times as much as the desired equivalent of iodine, and preferably it is equimolar to five times as much as the equivalent of iodine. Therefore, for example, in the case of the above recited potassium peroxodisulfate or sodium tosylchloramide, each content is within the range of about 0.0001 to about 0.5 mole/$m^2$, preferably 0.01 to 0.15 mole/$m^2$.

The above-mentioned iodine compound and oxidizing agent may be present in different layers or in one layer, and may be disposed at any position. However, it is preferred that they are disposed in different layers, and it is also preferred that they are sectioned and disposed between the starch and the support.

The analytical element of this invention can take an optional layer constitution in which a conventional developing layer and/or reagent layer is utilized. Examples of such constitutions are as follows: (1) a constitution is which the reagent layer including an oxidizing agent is provided on the liquid-impervious support, and the developing layer including a starch and an iodine compound is put thereon; (2) a constitution in which a first reagent layer including an oxidizing agent (or an iodine compound) is provided on the support, a second layer including the iodine compound (or the oxidizing agent) is put thereon, and the developing layer including a starch is further put thereon; (3) a constitution in which the reagent layer is provided on the support, the macromolecule-receiving reagent layer which has a mechanism for receiving a macromolecule such as protein is put thereon (e.g., see descriptions of Japanese Provisional Patent Publication No. 70163/1983 and Japanese Patent Application No. 6505/1982 published as Japanese Provisional Patent Publication No. 123458/1983), and the developing layer is provided thereon, an oxidizing agent being incorporated into the reagent layer, a starch being incorporated into the macromolecule-receiving layer and an iodine compound being incorporated into the macromolecule-receiving layer or the developing layer, respectively; (4) a constitution in which the reagent layer including an iodine compound and an oxidizing agent in the form of each different fine particles is provided on the support, and the developing layer including a starch is put thereon; (5) a constitution in which the peculiar binder layer is interposed between the developing layer and the reagent layer, in the constitution (4); (6) a constitution in which the reagent layer including an iodine compound and an oxidizing agent in the form of different fine particles is provided on the support, the macromolecule-receiving layer including a starch is put thereon, and the developing layer is further superimposed thereon; and (7) a constitution in which on the support, there is provided a layer including a starch, an iodine compound and an oxidizing agent in the form of each different fine praticles. In each constitution above, the iodine compound and the oxidizing agent must be distributed so that they may not react with each other to generate undesirable iodine before contacting with the fluid sample. In the constitutions (4) to (7) mentioned above, one or more components may be contained in layers, for example, in the form of micro-capsules.

When the above recited seven constitutions are compared with each other from the viewpoint of the reactivity of α-amylase, it will be understood that the analytical element having the layer constitution (2) is preferable.

Now, the support in the analytical element of this invention may be liquid-impervious and preferably light-transmissive. Examples of such supports include a variety of polymer materials such as cellulose acetate, polyethylene terephthalate, polycarbonate and polystyrene. In addition to these polymer materials, inorganic materials such as glass can be further employed. The thickness of the support is optional but is preferably within the range of about 50 to about 250 μm. One surface of the support through which an observation is carried out can be optionally treated in accordance with its purpose.

Examples of the developing layers used in the analytical element of this invention include a developing layer of a non-fibrous porous medium called "a brush polymer" composed of titanium dioxide and cellulose diacetate which is disclosed in Japanese Patent Publication No. 21677/1978, a developing layer made from a fabric which is disclosed in Japanese Provisional Patent Publication No. 164356/1980 etc., and a fibrous structure developing layer which is disclosed in Japanese Provisional Patent Publications No. 24576/1981, No. 125847/1982 and No. 197466/1982. Particularly, the above-mentioned fibrous structure developing layer has a mechanism for dealing a fluid sample to the reagent layer in uniform amounts per unit area and is especially useful as a material capable of allowing blood corpuscles to be forwarded smoothly therethrough. Further, the fibrous structure developing layer is also available to developmentally forward such a macromolecule as α-amylase which is the target of this invention.

The thickness of the developing layer in the analytical element of this invention should depend on its voids, but it is preferably within the range of about 100 to about 500 μm, more preferably within the range of about 150 to about 350 μm. Further, the voids mentioned above are preferably within the range of about 20 to about 85 %.

The analytical element of this invention can additionally include other additives such as an α-amylase-activating agent, a buffering agent, a surface active agent and a binder, if desired.

The α-amylase-activating agents include all kinds of chlorides, but the chlorides which have no hygroscopicity and which are hard to change their own properties are recommendable, and sodium chloride, potassium chloride and the like are preferred.

The amount of the chloride contained in the analytical element of this invention is generally within the range of 0.0003 to 1 mole/$m^2$, preferably 0.005 to 0.2 mole/$m^2$.

As the buffering agent, any one is acceptable so long as it has a strong buffering ability in the vicinity of pH 7.0 which is an optimum hydrogen ion concentration to the α-amylase, and is readily soluble, and the preferable buffering agents include phosphate buffering agents, β-glycerol phosphate buffering agents, 3-(N-morpholino)propane sulfonate buffering agent, [N-tris(hydroxymethyl)methyl]-2-aminoethane sulfonate buffering agent and the like. The content of the buffering agent included in the analytical element of this invention is generally within the range of 0.0001 to 1 mole/$m^2$, preferably within the range of 0.01 to 0.5 mole/$m^2$.

The surface active agent serves effectively to control a permeating speed of a fluid sample after the latter has been brought into contact with the analytical element of this invention. Further, an agent among them is effective only in the developing layer. The surface active agent usable regardless of being ionic (anionic or cationic) and being nonionic. These surface active agents have effects of controlling the permeating speed of a fluid sample toward the reagent layer and simultaneously restraining the occurence of an undesirably "chromatographic phenomenon".

The selectable amount of the surface active agent ranges extensively, and it is generally within the range of 10 to 0.005 % by weight, preferably 6 to 0.05 % by weight based on the weight of a coating solution.

The various additives mentioned above may be prepared in the form of fine powders and may be dispersed directly when used, but they may preferably be prepared in the form of solutions such as aqueous solutions and may be dispersed directly when used.

The binder is utilized to cause the layers to adhere to each other, therefore it is necessary for the developing layer but is not always required in the reagent layer. If used in the reagent layer, the binder is preferably a water-soluble binder except for the case where the above-mentioned macromolecule-receiving reagent layer or starch-including reagent layer is employed. The more preferable water-soluble binders are gelatin, polyacrylamide and polyvinyl pyrrolidone. Further, as the binders used in the aforesaid macromolecule-receiving reagent layer and the starch-including reagent layer, polymers which are hydrophilic and soluble in an organic solvent such as an alcohol, for example, polyvinylpyrrolidone are preferred. The binders used in the developing layer are not limited particularly, but the hydrophobic binders are more preferred.

The binder is preferably dissolved in a solvent when used, and its amount is not limited. In the case that the binder is employed in the starch-including layer, however, its amount is, in a weight ratio, 0 to 20 times, preferably 0.5 to 10 times as much as that of the starch.

The peculiar binder layer in the layer constitution (5) mentioned above is provided so as to gradually release iodine from the reagent layer in accordance with the reaction of the α-amylase in a fluid sample with the starch in the developing layer. Such a peculiar binder layer is suitably made of a polymeric material comprising about 60 to 100 mole % of a hydrophilic monomer and about 40 to 0 mole % of a hydrophobic monomer. Examples of such polymeric materials include polyacrylamide, polymethacrylamide, polyisopropylacrylamide, polybutylacrylamide and acrylamide/n-butyl acrylate (90:10 in a molar ratio) copolymers.

When micro-capsules are employed in the layer constitutions (4) to (7) mentioned above, in the case that their wall material includes a starch, hydrophilic polymeric materials typically such as gelatin and water-soluble cellulose derivatives are preferred; in the case that their wall material includes an iodine compound or an oxidizing agent, water-insoluble polymeric materials which can allow the iodine compound or the oxidizing agent to be released through their voids are preferred.

Each additives mentioned above may be added to the layer including the iodine compound and/or the oxidizing agent and/or the starch, but may be caused to exist in a newly prepared layer.

The analytical element of this invention can optionally be combined with, for example, a reflective layer or an undercoat layer disclosed in the specification of U.S. Pat. No. 3,992,158, or a barrier layer disclosed in the specification of U.S. Pat. No. 4,066,403, if desired, so as to fit the object of this invention.

For example, in the layer constitution (1) or (4), the reflective layer may be interposed between the reagent layer and the support, or may be caused to simultaneously have a mechanism of the reagent layer. In this constitution, when an optical photometry is carried out from the side of the developing layer, the difference in an optical density will be great and a distinguishing power can be thus improved.

Further, it is preferred that the light-transmissive undercoat layer is provided on the support, because adhesion properties between the support and a layer adjacent thereto can be heightened.

The respective layers consisting the analytical element of this invention can be superimposed in turn over the support in accordance with a desired layer constitution by suitably selecting a slide hopper coating method, an extrusion coating method, an immersion coating method or the like which are now known in the field of a photographic industry, in order to obtain the analytical element having an optional thickness.

According to this invention, the amount of a specific component in a fluid sample can be measured from the side of the support or the opposite side thereto by means of a reflected spectrum photometry with the aid of an initial velocity process or a reaction terminating process. The thus measured values will be compared with a previously prepared calibration curve, thereby determining the amount of the specific component.

The amount of a used fluid sample for which the analytical element of this invention is utilized is optionally decided, but the preferable amount is within the range of about 5 to about 50 μl, and the more preferable amount is within the range of about 5 to about 20 μl. Generally, it is preferred to use about 10 μl of the fluid sample.

The analytical element of this invention can be utilized for whole blood, serum and blood plasma without any inconvenience. Further, urine and other body fluids can be likewise applied without any problems. In the case of employing the whole blood, a radiation blocking layer or another reflective layer may be additionally provided, if desired, for the purpose of avoiding the fact that the passage of the radiation for detection is interfered by hemocytes in the whole blood.

The analytical reaction utilized in the analytical element of this invention can be optionally decided in accordance with its purpose, and such a reaction is available in the field of a clinical chemistry and is employed for the analysis of components, particularly, in a biological fluid sample, i.e. blood or urine.

In the analytical element of this invention, iodine is separated into two of an iodine compound and an oxidizing agent and is contained in the binder or the micro-capsules. Therefore, no iodine will be sublimated and the deterioration of the iodine will not be brought about by light at all, in contrast to the analytical element directly including the iodine. In consequence, the storability of the iodine in the analytical element of this invention can seemingly be improved. Moreover, the analytical element of this invention has the function of generating the iodine in a solid phase, therefore less attention to the corrosion of the iodine is merely required than in the case of the wet chemistry.

In the analytical element of this invention, no iodine simple substance is present before brought into contact with a fluid sample, but when the sample is dropped, the iodine will diffuse gradually into an α-amylase-starch reaction zone and will form an iodine-starch complex therein in order to develop a color. Thus, the analytical element of this invention has the advantage that the obstacle function of the iodine to the α-amylase can be relieved to a substantial degree.

In addition thereto, in the analytical element of this invention, the iodine-starch complex which will develop a color when the fluid sample is dropped thereonto is a non-diffusible substance, therefore the analytical element of this invention also has the advantage that chromatographic phenomenon will scarcely appear and an ununiformed concentration will hardly be given.

In the following, this invention will be described in detail in reference to examples, but they do not intend to limit the scope of embodiments regarding this invention.

EXAMPLE 1

(A) Preparation of coating solutions (a) In 80 ml of distilled water were dissolved 5 g of gelatin, 1 g of sodium triisopropylnaphthalene sulfonate, 0.37 g of sodium chloride, 0.68 g of monopotassium phosphate and 0.27 g of potassium peroxodisulfate, and a pH of the resulting mixture was then adjusted to 7.0 with a 0.5 mole/l aqueous sodium hydroxide solution. Afterward, 0.1 g of 1,2-bis(vinylsulfonyl)ethane was added thereto, and distilled water was then added thereto to bring its total amount to 100 ml, whereby a coating solution for a reagent layer was prepared.

(b) To 140 ml of xylene were added 7.5 g of styreneglycidyl methacrylate copolymer (9:1 in a molar ratio) and 5 g of Triton X-100 [manufactured by Rohm & Haas Inc.] to prepare a xylene solution. A soluble starch [Zulkowsky starch; manufactured by Merck Co., Ltd.; Art. 1257] was passed through a 500-mesh sieve and potassium iodide was also passed through a 300-mesh sieve in order to obtain a soluble starch powder having a particle size of 500 mesh or more and a potassium iodide powder having a particle size of 300 mesh or more. Then, 2.5 g and 2.49 g of the thus obtained starch powder and potassium iodide powder respectively were added to the previously prepared xylene solution. To this mixture were added 50 g of a powdery filter paper C [manufactured by Toyo Roshi Co., Ltd, 300 mesh or more], followed by enough stirring to prepare a coating solution for a developing layer.

(B) Manufacture of analytical elements

A transparent undercoated polyethylene terephthalate support having a thickness of about 180 μm was coated thereon in turn with the coating solutions prepared in the preceding paragraphs (a) and (b) to manufacture analytical elements of this invention.

The composition of each layer constituting the analytical element of this invention is as follows:

| (a) Reagent layer A layer containing: | |
|---|---|
| Gelatin | 12.5 g/m$^2$ |
| Triton X-100 | 2.5 g/m$^2$ |
| Sodium chloride | 0.925 g/m$^2$ |
| Monopotassium phosphate | 1.7 g/m$^2$ |
| Potassium peroxodisulfate | 0.675 g/m$^2$ |
| 1,2-Bis(vinylsulfonyl)ethane | 0.25 g/m$^2$ |
| (b) Developing layer A layer containing: | |
| Powdery filter paper C | 104.17 g/m$^2$ |
| Soluble starch | 5.208 g/m$^2$ |
| Potassium iodide | 5.188 g/m$^2$ |
| Triton X-100 | 10.417 g/m$^2$ |
| Styrene-glycidyl methacrylate (9:1) copolymer | 15.625 g/m$^2$ |

Onto the thus manufactured analytical elements of this invention were dropped 10 μl of human sera each including 20 to 1000 Somogyi Unit (SU) of α-amylase, and they were maintained at 37° C. for 7.5 minutes. Then, a reflective optical density was measured at 660 nm. The α-amylase activity and the reflective optical density were in a good correlation, which fact elucidated that the analytical element of this invention would enable the quantitative determination of the α-amylase activity.

EXAMPLE 2

1. Manufacture of analytical elements of this invention (A) Preparation of coating solutions (a) In 80 ml of distilled water were dissolved 5 g of gelatin, 1 g of Triton X-100, 0.37 g of sodium chloride, 0.68 g of monopotassium phosphate and 2.075 g of potassium iodide, and a pH of the resulting mixture was then adjusted to 7.0 with a 0.5 mole/l aqueous sodium hydrocide solution. Afterward, 0.1 g of 1,2-bis(vinylsulfonyl)ethane was added thereto, and distilled water was then added thereto to bring its total amount to 100 ml, whereby a coating solution for a reagent layer - 1 was prepared.

(b) In 91.1 ml of 1,1,2,2-tetrachloroethane were dissolved 5 g of polyvinylpyrrolidone [manufactured by BASF, Kollidon-90] and 0.5 g of Triton X-100, and 3.38 g of potassium peroxodisulfate were then added thereto. Afterward, stirring was carried out by the use of a sand grinder for 4 hours in order to prepare a coating solution for a reagent layer - 2.

(c) To 140 ml of xylene were added 7.5 g of styreneglycidyl methacrylate copolymer (9:1 in a molar ratio) and 5 g of Triton X-100 to prepare a xylene solution. A soluble starch [Zulkowsky starch] was passed through a 500-mesh sieve in order to obtain a soluble starch powder having a particle size of 500 mesh or more. Then, 2.5 g of the thus obtained soluble starch powder were added to the previously prepared xylene solution. To this mixture were afterward added 50 g of a powdery filter paper C, followed by enough stirring to prepare a coating solution for a developing layer.

(B) Manufacture of analytical elements

A transparent undercoated polyethylene-terephthalate support having a thickness of about 180 μm was coated thereon in turn with the coating solutions prepared in the preceding paragraphs (a), (b) and (c) to manufacture analytical elements of this invention.

The composition of each layer constituting the analytical element of this invention is as follows:

| (a) Reagent layer - 1 A layer containing: | |
|---|---|
| Gelatin | 12.5 g/m$^2$ |
| Triton X-100 | 2.5 g/m$^2$ |
| Sodium chloride | 0.925 g/m$^2$ |
| Monopotassium phosphate | 1.7 g/m$^2$ |
| Potassium iodide | 5.188 g/m$^2$ |
| 1,2-Bis(vinylsulfonyl)ethane | 0.25 g/m$^2$ |
| (b) Reagent layer - 2 A layer containing: | |
| Polyvinylpyrrolidone | 5 g/m$^2$ |
| Triton X-100 | 0.5 g/m$^2$ |
| Potassium peroxodisulfate | 3.38 g/m$^2$ |
| (c) Developing layer A layer containing: | |
| Powdery filter paper C | 104.17 g/m$^2$ |
| Soluble starch | 5.208 g/m$^2$ |
| Triton X-100 | 10.417 g/m$^2$ |
| Styrene-glycidyl methacrylate (9:1) copolymer | 15.625 g/m$^2$ |

2. Manufacture of analytical elements for comparison (A) Preparation of coating solutions (a) In 60 ml of distilled water were dissolved 5 g of gelatin, 1 g of Triton X-100, 0.37 g of sodium chloride and 0.68 g of monopotassium phosphate, and 25 ml of a 0.05 mole/l iodine-potassium iodide solution were then added thereto. Then, a pH of the resulting mixture was adjusted to 7.0 with a 0.5 mole/l aqueous sodium hydroxide solution. Afterward, 0.1 g of 1,2-bis(vinylsulfonyl)ethane was added thereto, and distilled water was then added thereto to bring its total amount to 100 ml, whereby a coating solution for a reagent layer - 1 was prepared.

(b) In 94.5 ml of 1,1,2,2-tetrachloroethane were dissolved 5 g of polyvinylpyrrolidone and 0.5 g of Triton X-100 in order to prepare a coating solution for a reagent layer - 2.

(B) Manufacture of analytical elements

A transparent undercoated polyethylene-terephthalate support having a thickness of about 180 μm was coated thereon in turn with the coating solutions prepared in the preceding paragraphs (a) and (b) in order to manufacture analytical elements for comparison.

The compositions of each layer constituting the analytical element for comparison is as follows:

| (a) Reagent layer - 1 A layer containing: | |
|---|---|
| Gelatin | 12.5 g/m$^2$ |
| Triton X-100 | 2.5 g/m$^2$ |
| Sodium chloride | 0.925 g/m$^2$ |
| Monopotassium phosphate | 1.7 g/m$^2$ |
| Iodine-potassium iodide | 0.00313 mole/m$^2$ |
| 1,2-Bis(vinylsulfonyl)ethane | 0.25 g/m$^2$ |
| (b) Reagent layer - 2 A layer containing: | |
| Polyvinylpyrrolidone | 5 g/m$^2$ |
| Triton X-100 | 0.5 g/m$^2$ |
| (c) Developing layer A layer containing: | |
| Powdery filter paper C | 104.17 g/m$^2$ |
| Soluble starch | 5.208 g/m$^2$ |
| Triton X-100 | 10.417 g/m$^2$ |
| Styrene-glycidyl methacrylate (9:1) copolymer | 15.625 g/m$^2$ |

Making observations between the thus manufactured analytical element of this invention and analytical element for comparison, it was found that the former element was white but the latter element was yellow. Further, when reflective optical densities were measured at 450 nm from the sides of developing layers, values of 0.065 and 0.528 were obtained for the analytical element of this invention and the analytical element for comparison, respectively, which results indicated that the developing layer in the analytical element of this invention included no iodine, but the developing layer in the analytical element for comparison already included the same.

Figure 1:
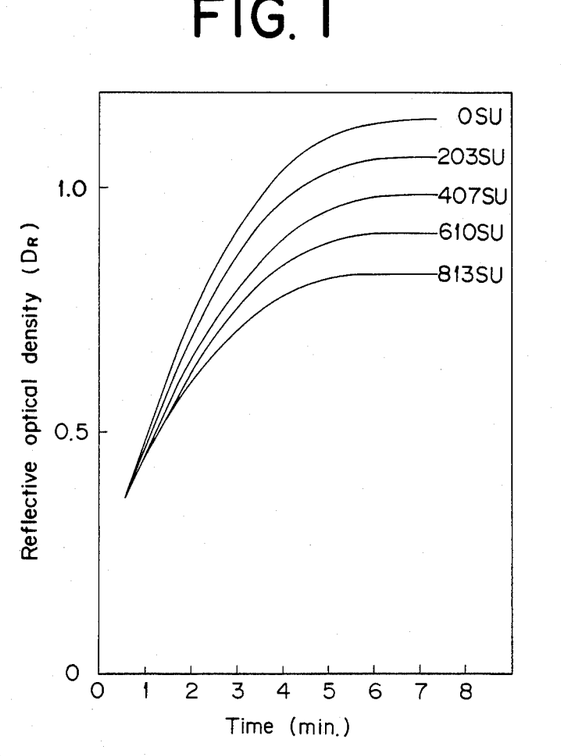
FIGS. 1 and 2 are graphs showing relations between times and reflective optical densities of an analytical element of this invention and an analytical element for comparison, respectively.
Figure 2:
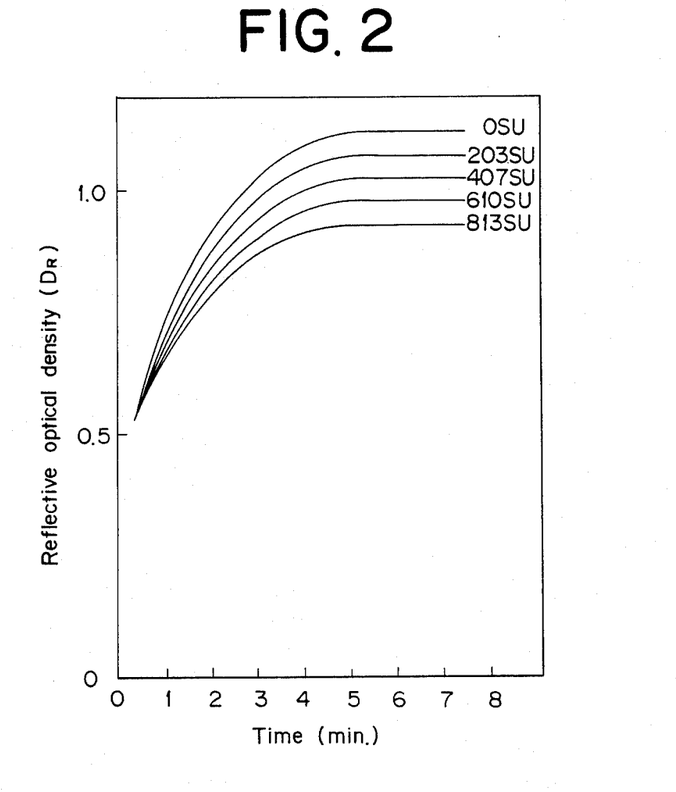

These respective analytical elements were spotted with 10 μl of a solution of 1 % α-amylase originated from human saliva in bovine serum albumin, and were then maintained at 37° C. for 7.5 minutes. Afterward, the reflective optical concentrations at 660 nm were measured at an interval of 30 seconds. The results are shown in FIG. 1 below which is connected with the analytical elements of this invention and in FIG. 2 which is the analytical elements for comparison respectively, each drawing being a graph showing a relation between time (minutes) (abscissa axis) and the reflective optical density $D_R$ (ordinate axis). In these drawings, the amounts of the α-amylase are shown on each curve with Somogyi Unit (SU). As is definite from the respective drawings, the analytical elements for comparison exhibited values of high $D_R$ immediately after dozens of seconds had lapsed from a point of the spotting time, and reached a maximum value D after about 5 minutes. On the contrary, the analytical elements of this invention exhibited much lower DR values within dozens of seconds after the spotting operation than the analytical elements for comparison, and reached a maximum value $D_R$ after about 6 minutes had passed. Hence, it is apparent therefrom that the constitution where iodine is indirectly contained in the analytical element in the form of an iodine compound and an oxidizing agent enables inhibiting the diffusion of the iodine (an obstacle material at the time of the layer formation) into the developing layer which is the reactive zone of the α-amylase, unlike the constitution where the iodine is directly contained in the analytical element in the form of an iodine simple substance.

Figure 3:
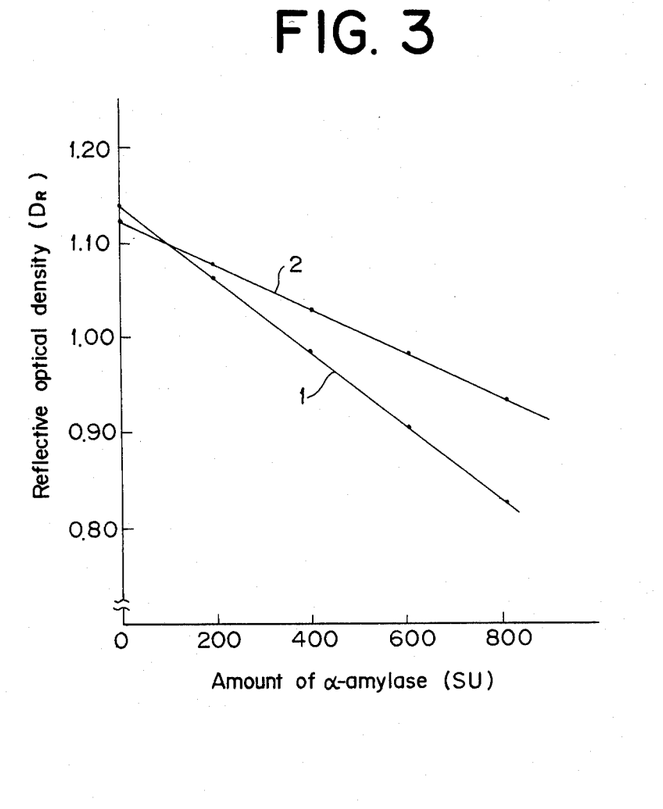
FIG. 3 is a graph showing a relation between an amount of α-amylase and a reflective optical density.

Therefore, in the analytical element of this invention, an obstacle function of the iodine to the α-amylase could be relieved more than in the analytical element for increased, with the result that an identification power for the α-amylase on the basis of the DR was enhanced. In FIG. 3, there is shown a graph illustrating a relation between the amount (SU) of the α-amylase (abscissa axis) and the reflective optical density (DR) (ordinate axis), and 1 is an analytical element of this invention and 2 is an analytical element for comparison.

TABLE 1

| α-Amylase (SU) | 0 | 203 | 407 | 610 | 813 |
|---|---|---|---|---|---|
| $D_R$ after 7 minutes | | | | | |
| Analytical element of this invention | 1.141 | 1.063 | 0.984 | 0.905 | 0.826 |
| Analytical element for comparison | 1.123 | 1.077 | 1.030 | 0.983 | 0.935 |

Moreover, the analytical element of this invention and the analytical element for comparison were stored at 60° C. for 30 days for the purpose of inspecting the retention of an iodine generating ability in the analytical element of this invention and the stability of the iodine in the analytical element for comparison. The results were that the former was 99.5 % or more and the latter was 80 %.

Accordingly, it has been elucidated from the results that the retention of the iodine generating ability in the analytical element of this invention is better than the storability of the iodine in the analytical element for comparison.

As described above in detail, according to the analytical element of this invention, the iodine is included in the analytical element in the form of an iodine compound and an oxidizing agent. Therefore, the retention of the iodine generating ability can be improved, the identification power for the α-amylase can be built up, and ununiformed coloring and chromatography phenomenon scarcely appear. Further, the analytical element of this invention enables an easy, prompt and accurate dry quantitative analysis of a component in a fluid sample, especially, a biological fluid sample by the use of visible light with the aid of a usual spectrophotometer, and the analytical element of this invention is thus considered to be highly practical and convenient.

We claim:

1. A dry analytical element for α-amylase in a fluid sample comprising a starch capable of forming a complex with iodine, and iodine compound and an oxidizing agent, wherein said oxidizing agent is capable of reacting with said iodine compound to generate iodine and said iodine compound and said oxidizing agent are disposed in said element so that iodine may be liberated therefrom when said fluid sample is brought into contact with said analytical element.

2. The dry analytical element for α-amylase of claim 1, wherein said iodine compound or said oxidizing agent or both said iodine compound and said oxidizing agent, are dispersed in said element in the form of particles.

3. The dry analytical element for α-amylase of claim 1, wherein said iodine compound or said oxidizing agent or both said iodine compound and said oxidizing agent, are dispersed in said element in the form of microcapsules.

4. The dry analytical element for α-amylase of claim 1, wherein said starch is selected from the group consisting of a soluble starch and an amylose.

5. The dry analytical element for α-amylase of claim 4, wherein said starch is included in the analytical element within the range of about 0.1 to about 50 g/m$^2$.

6. The dry analytical element for α-amylase of claim 1, wherein said iodine compound is selected from the group consisting of a tetramethylammonium iodide and tetraethylammonium iodide.

7. The dry analytical element for α-amylase of claim 6, wherein said iodine compound is included, in terms of iodine ion, in the analytical element within the range of about 0.0003 to about 5 moles/m$^2$.

8. The dry analytical element for α-amylase of claim 1, wherein said oxidizing agent is selected from the group consisting of potassium peroxodisulfate and sodium tosylchloramide.

9. The dry analytical element for α-amylase of claim 8, wherein said oxidizing agent is included in the analytical element within the range of about 0.0001 to about 0.5 moles/m$^2$.

10. The dry analytical element for α-amylase of claim 1, wherein said analytical element comprises a reagent layer including the oxidizing agent provided on a liquid-impervious support, and a developing layer including the starch and the iodine compound formed on said reagent layer.

11. The dry analytical element for α-amylase of claim 1, wherein said analytical element comprises a first reagent layer including the oxidizing agent provided on a liquid impervious support, a second layer including the iodine compound on said first reagent layer and a developing layer including the starch formed on said second layer.

12. The dry analytical element for α-amylase of claim 11, wherein said analytical element comprises a reagent layer provided on a liquid-impervious support, a macromolecule-receiving reagent layer for receiving a macromolecule formed on said reagent layer, and a developing layer provided on said macromolecule receiving reagent layer, the oxidizing agent being incorporated into the reagent layer, the starch being incorporated into the macromolecule-receiving layer and the iodine compound being incorporated into the macromolecule-receiving layer or the developing layer, respectively.

13. The dry analytical element for α-amylase of claim 1, wherein said analytical element comprises a reagent layer including the iodine compound and the oxidizing agent in the form of different particles provided on a liquid-impervious support, and a developing layer including the starch formed on said reagent layer.

14. The dry analytical element for α-amylase of claim 13, wherein said analytical element comprises a binder layer interposed between the developing layer and the reagent layer.

15. The dry analytical element for α-amylase of claim 1, wherein said analytical element comprises a reagent layer including the iodine compound and the oxidizing agent in the form of different particles provided on a liquid-impervious support, a macromolecule-receiving layer including the starch formed on said reagent layer and a developing layer further superimposed on said macromolecule-receiving layer.

16. The dry analytical element for α-amylase of claim 1, wherein said analytical element comprises a liquid-impervious support and a layer including the starch, the iodine compound and the oxidizing agent in the form of different particles provided on said layer.

17. The dry analytical element for α-amylase of claim 2, wherein
said starch is in an amount of about 0.1 to about 50 g/m$^2$ and said starch is selected from the group consisting of a soluble starch and an amylose;
said iodine compound in terms of the iodine ion is in the amount of about 0.0003 to about 5 moles/m$^2$;
said iodine compound is one selected from the group consisting of tetraethylammonium iodide and tetramethylammonium iodide;
said oxidizing agent is about 0.000to about 0.5 moles/m$^2$; and
said oxidizing agent is selected from the group consisting of potassium peroxodisulfate and sodium tosylchloramide.

18. The dry analytical element for α-amylase of claim 1, wherein
said starch is in an amount of about 0.1 to about 50 g/m$^2$ and said starch is selected from the group consisting of a soluble starch and an amylase;
said iodine compound in terms of the iodine ion is in the amount of about 0.0003 to about 5 moles/m$^2$;
said iodine compound is one selected from the group consisting of tetramethylammonium iodide and tetraethylammonium iodide;
said oxidizing agent is about 0.0001 to about 0.5 moles/m$^2$;
said oxidizing agent is selected from the group consisting of potassium peroxodisulfate and sodium tosylchloramide; and
said iodine compound or said oxidizing agent or both said iodine compound and said oxidizing agent are dispersed in said element in the form of microcapsules.

19. The dry analytical element for α-amylase of claim 18, wherein said analytical element comprises a reagent layer provided on a liquid-impervious support, a macromolecule receiving reagent layer for receiving a macromolecule formed on said reagent layer, and a developing layer provided on said macromolecule-receiving reagent layer, the oxidizing agent being incorporated into the reagent layer, the starch being incorporated into the macromolecule-receiving layer and the iodine compound being incorporated into the macromolecule-receiving layer or the developing layer, respectively.

20. The dry analytical element for α-amylase of claim 18, wherein said analytical element comprises a reagent layer including the iodine compound and the oxidizing agent provided on a liquid-impervious support, a macromolecule-receiving layer including the starch formed on said reagent layer, and a developing layer superimposed on said macromolecule-receiving layer.

21. The dry analytical element for α-amylase of claim I wherein said analytical element comprises a first layer provided on a liquid-impervious support and including the iodine compound; a reagent layer including the oxidizing agent formed on said first layer; and a developing layer including the starch formed on said reagent layer.

* * * * *